Figure 1:
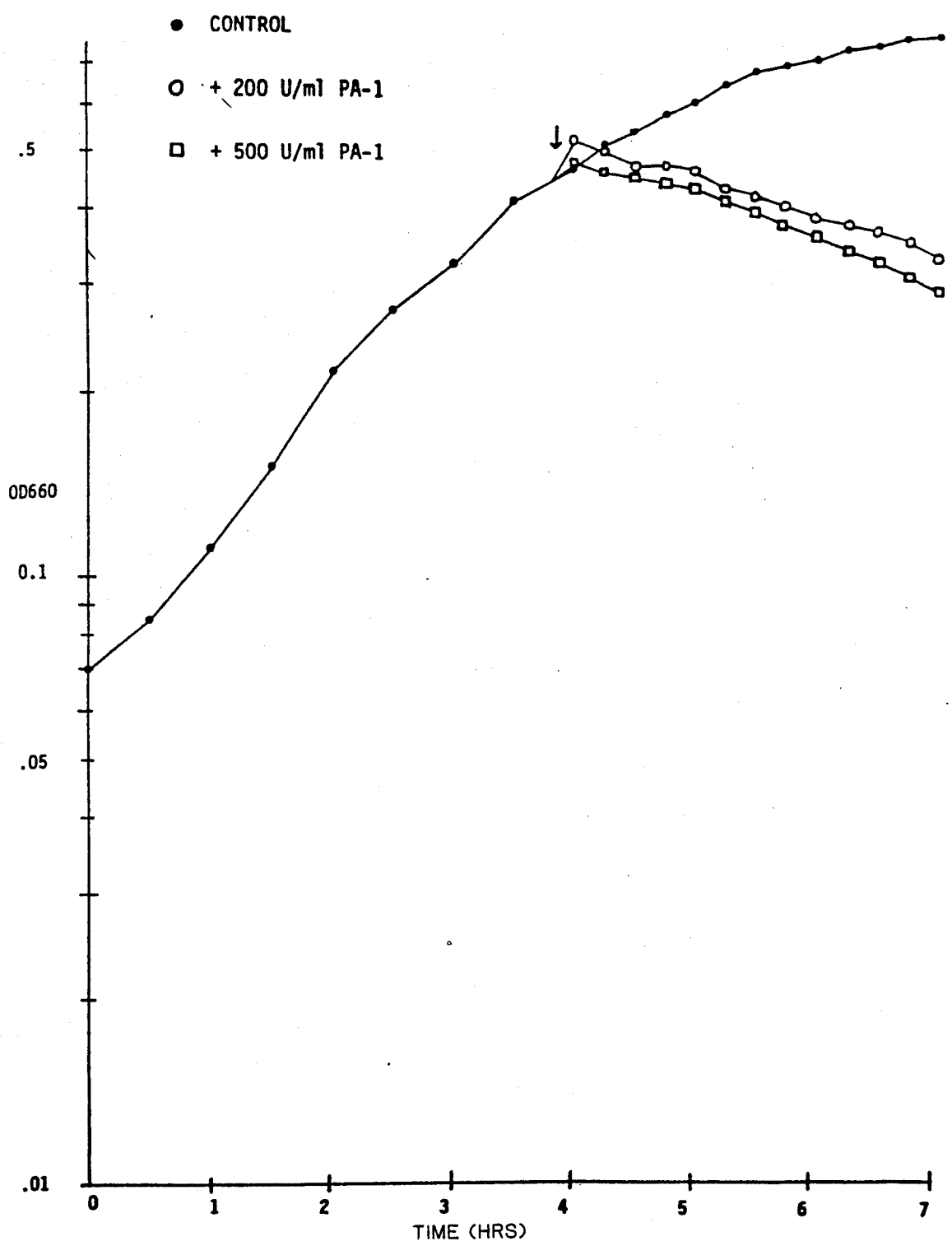

United States Patent [19]

Vandenbergh et al.

[11] Patent Number: 4,929,445

[45] Date of Patent: * May 29, 1990

[54] **METHOD FOR INHIBITING *LISTERIA MONOCYTOGENES* USING A BACTERIOCIN**

[75] Inventors: Peter A. Vandenbergh; Michael J. Pucci, both of Sarasota; Blair S. Kunka, Bradenton; Ebenezer R. Vedamuthu, Bradenton, all of Fla.

[73] Assignee: Microlife Technics, Inc., Sarasota, Fla.

[*] Notice: The portion of the term of this patent subsequent to May 23, 2006 has been disclaimed.

[21] Appl. No.: 148,044

[22] Filed: Jan. 25, 1988

[51] Int. Cl.$^5$ .................... A01N 59/00; A01N 65/00; A23C 9/12
[52] U.S. Cl. .................... 424/115; 424/195.1; 426/38; 426/61; 435/170; 435/252.9; 435/822; 435/835
[58] Field of Search ............... 424/195.1, 115; 426/38, 426/61; 435/252.9, 170, 822, 853

[56] References Cited

PUBLICATIONS

Tagg et al., Bacteriol. Rev. 40: 722–756 (1976).
Gonzalez et al., Appl. Environ. Microbiol. 53: 2534–2538 (1987).
McLauchlin, J., J. Applied Bact. 63: 1–11 (1987).
Bergey's Manual of Systematic Bacteriology, vol. 2: 1235–1245 (1986).
Gonzalez et al., Appl. Environ. Microbiol. 46: 81–89 (1983).

*Primary Examiner*—John W. Rollins
*Attorney, Agent, or Firm*—Ian C. McLeod

[57] ABSTRACT

A method for inhibiting *Listeria monocytogenes* in a food or other material which can be contaminated with this pathogen using a bacteriocin produced by DNA in *Pediococcus acidilactici* is described. The bacteriocin is particularly produced by *Pediococcus acidilactici* containing a 6.2 Mdal (9.4 Kilobase pairs) plasmid encoding for the bacteriocin.

26 Claims, 2 Drawing Sheets

METHOD FOR INHIBITING *LISTERIA MONOCYTOGENES* USING A BACTERIOCIN

BACKGROUND OF THE INVENTION

(1) Summary of the Invention

The present invention relates to a method for inhibiting *Listeria monocytogenes*, a foodborne pathogen, in a food or other materials which can be contaminated by this pathogen using a bacteriocin. In particular the present invention relates to the use of a bacteriocin derived from *Pediococcus acidilactici* to inhibit the *Listeria monocytogenes* in the food or other materials which can be contaminated by this pathogen.

(2) Prior Art

The term "bacteriocin" refers to a protein of the colicin type, characterized by lethal biosynthesis by the producing bacterium, intraspecific activity in related species of bacteria, and adsorption to specific receptors on the sensitive bacteria (Tagg, J. R., A. S. Dajani, and L. W. Wannamaker, Bacteriol. Rev. 40:722–756 (1976)). Bacteriocins have been described as being produced by many bacteria, however the bacterial strains inhibited by the bacteriocin are usually related to the strain which produces the bacteriocin (Gonzalez, C. F., and B. S. Kunka, Appl. Environ. Microbiol. 53:2534–2538 (1987)).

In U.S. Pat. No. 4,883,673, filed Feb. 9, 1987 by Carlos Gonzalez, which is assigned to a common assignee, the preparation and use of a bacteriocin derived from *Pediococcus acidilactici*, particularly *Pediococcus acidilactici* NRRL-B-18050, to inhibit spoilage bacteria, particularly *Lactobacillus fermentum* and *Lactobacillus bifermentum*, is described. These spoilage bacteria are lactic acid producing strains of the genus *Lactobacillus* and *Pediococcus*. No activity was found against *Lactococcus lactis*, *Lactococcus lactis* subsp. *diacetylactis*, *Lactococcus cremoris* (previously in the genus "Streptococcus") or *Streptococcus thermophilus*, *Staphylococcus aureus*, *Micrococcus varians*, *Micrococcus sodonensis*, *Staphylococcus xylosus*, *Staphylococcus epidermidis*, *Staphylococcus carnosus*, *Lactobacillus acidophilus*, *Lactobacillus lactis* and *Lactobacillus bulgaricus*. It was concluded that the bacteriocin had a limited range of inhibitory activity related to gram positive, lactic acid bacteria.

*Listeria monocytogenes* has been demonstrated to be transmitted in contaminated food. (J. Applied Bact. 63:1–11 (1987)). While the culture is sensitive to pH and an acid environment will usually inhibit the growth of this microorganism, there are many instances of foods where the pH is not sufficiently acidic.

*Listeria monocytogenes* produces severe illness in animals and humans. The characteristics of the disease and this species are described in J. Applied Bact. 63:1–11 (1987). *Listeria monocytogenes* grows well at refrigeration temperatures and thus usual means of inhibiting the growth of *Listeria monocytogenes* by refrigeration is ineffective. Because of this there are problems in the marketplace, an example of which is the recently published recall of several brands of Listeria contaminated ice cream bars. Accoding to *Bergey's Manual of Systematic Bacteriology*, Vol 2: 1235–1245, (1986), the taxonomic position of the genus Listeria with regard to other genera is still not resolved. However, it is clear that *Listeria monocytogenes* is quite distinct from Lactobacillus, Staphylococcus, Micrococcus, Pediococcus and Streptococcus (Lactococcus).

OBJECTS

It is therefore an object of the present invention to provide a method for inhibiting *Listeria monocytogenes* in foods and other materials which can be contaminated by this pathogen using a bacteriocin. Further, it is an object of the present invention to provide a method which is simple and economical to perform. These and other objects will becomes increasingly apparent by reference to the following description and the drawings.

IN THE DRAWINGS

FIG. 1 shows the effect of addition of a powder containing the bacteriocin, designated PA-1, from *Pediococcus acidilactici* to an exponentially growing *Listeria monocytogenes* culture. The PA-1 powder was added to a *L. monocytogenes* culture at 200 U(units)/ml or 500 U/ml and turbidity (which is an indicator of the number of cells) was monitored over time at 660 nanometers. The symbols used are ○, control (no PA-1 added); ●, 200 U/ml PA-1; □, 500 U/ml PA-1.

Figure 2:
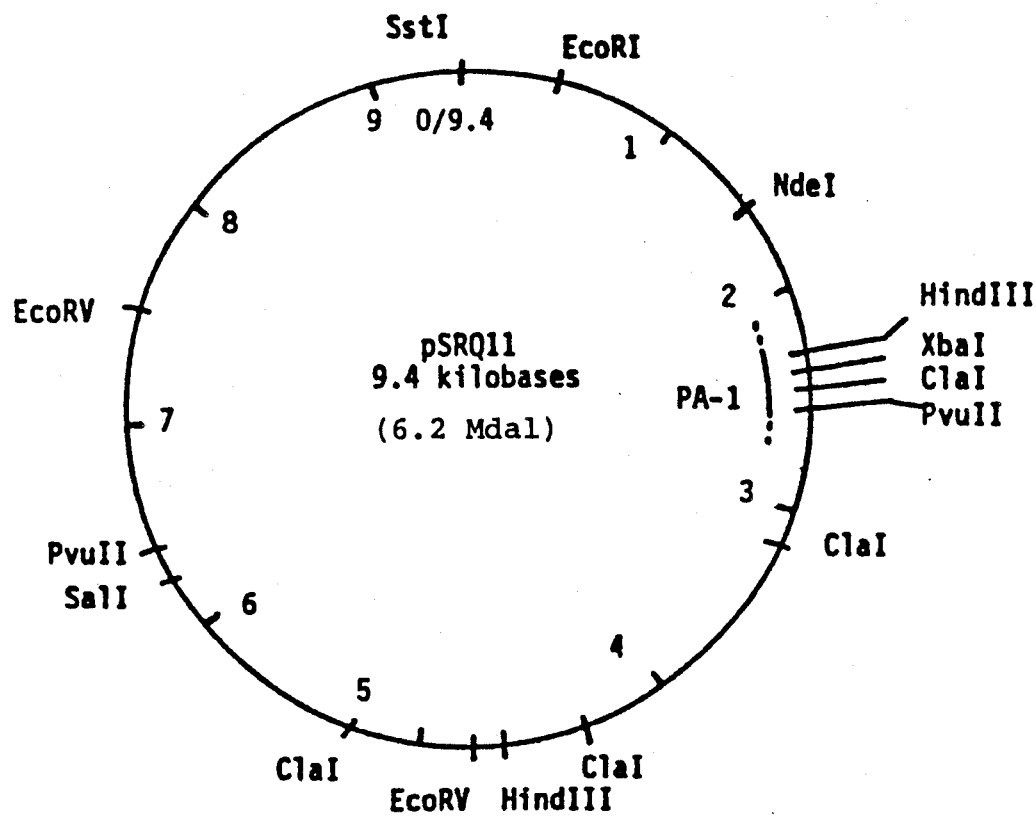

FIG. 2 shows a restriction endonuclease map of plasmid pSRQ11 which encodes for the production of the bacteriocin PA-1 in *Pediococcus acidilactici* NRRL-B-18050 (also known as PAC 1.0). Plasmid pSQ11, having a size of 9.4 kilobases, is shown with the locations of several restriction endonuclease sites. The approximate location of the coding region of bacteriocin PA-1 gene is shown. Four restriction sites were found within the PA-1 gene: HindIII, Xba I, Cla I, and PvuII.

GENERAL DESCRIPTION

The present invention relates to a method for inhibiting growth of *Listeria monocytogenes* in a material which is a food or other material which can be contaminated with the *Listeria monocytogenes* which comprises: providing a bacteriocin obtained from DNA which encodes for the bacteriocin in *Pediococcus acidilactici* in the material in an effective amount which inhibits the *Listeria monocytogenes*.

The present invention relates to a method for inhibiting growth of *Listeria monocytogenes* in a food which can contain the *Listeria monocytogenes* as a contaminant which comprises: adding a bacteriocin obtained from a bacterium containing DNA which encodes for the bacteriocin in *Pediococcus acidilactici* into the food in an effective amount which inhibits the *Listeria monocytogenes*. A preferred bacteriocin is PA-1

The preferred bacteriocin PA-1 used in the present invention is produced by *Pediococcus acidilactici* NRRL-B-18050, which is deposited with the Northern Regional Research Laboratory in Peoria, Illinois and is also known herein as PAC 1.0. *Pediococcus acidilactici* is a commercially available species used in meat fermentations. This preferred spcies contains a 9.4 kilobase (6.2 Mdal) plasmid which encodes for the bacteriocin. Using well known recombinant genetic techniques, the DNA gene segment encoding for the bacteriocin can be cut and combined with vector DNA and then inserted into another microorganism which then produces the bacteriocin.

The easiest method for providing the bacteriocin, such as PA-1, is to dry the growth medium containing the bacteriocin after cell growth to produce a powder. The solid materials can be removed by filtration or centrifugation from the growth medium. Low molecular weight compounds can be removed by membrane filtration, particularly reverse osmosis. Food grade drying aids such as non-fat dry milk (NFDM) can be used to dry the solution containing the bacteriocin. The bacteriocin is a proteinaceous material and can also be separated from the growth medium by precipitation or by other well known techniques such as reverse osmosis and it can then be dried in a pure form. The bacteriocin has a molecular weight of about 16,500 daltons and is inactivated by in vitro mixing with protease, papain or alpha-chymotrypsin and is unaffected by phospholipase C, lysozyme, Dnase and RNase or heating to 100° C. in water and inhibits *Listeria monocytogenes* in a pH range between about pH 4 to 9. The preparation of the bacteriocin and its characteristics are described in U.S. Pat. No. 4,883,673.

The bacteriocin is preferably used in the food system in an amount between 1 and 1,000,000 Arbitrary Units (AU) of bacteriocin, such as PA-1, per gram of the food. One AU of bacteriocin was defined as 5 microliters of the highest dilution of culture supernatant yielding a definite zone of growth inhibition with a lawn of an indicator strain of a gram-positive bacteria on an agar plate (*Pediococcus pentosaceus* FBB-63 formerly known as *Pediococus cerevisiae* FBB-63).

The foods most often associated with contamination by *Listeria monocytogenes* are milk based cheeses, ice cream of ice milk and Cottage cheese. Foods that are handled by machinery and are not heat-treated in final package are particularly vulnerable. Meats, such as beef, pork or poultry, can be contaminated during or after slaughtering. Fish can also be contaminated in processing.

Medicinal and veterinary products including packaging, lubricants, bandages, culture media and the like can be contaminated with *Listeria monocytogenes*. Further, cosmetics and other related products can be contaminated with this pathogen. The bacteriocin derived from *Pediococcus acidilactici* is useful for inhibiting this pathogen in these products, although the risk is greatest in foods and other products taken orally. All of these products can come in contact with living tissue in vitro or in vivo and can cause disease.

SPECIFIC DESCRIPTION

The methods and materials used for the production of the bacteriocin were as follows:

Bacterial Strain. *Pediococcus acidilactici* NRRL-B-10850, was routinely grown at 35° C. and cultivated on MRS broth (Difco, Detroit, Mich.).

Bacteriocin assay. Production of bacteriocin was assayed by spotting cells or filter sterilized broth samples onto MRS agar (Difco Laboratories, Detroit, Mich.). Filter sterilized broth samples were diluted by serial dilution (1:1, 1:2, 1:4, 1:8, 1:16, in sterile water) to titer the level of activity. Assay plates were overlaid with soft agar (0.75%) seeded with indicator cells (*Pediococcus pentosaceus* FBB63C). Plates were incubated at 32° C. for 18 hours.

EXAMPLE 1

Nutritional Studies

Each of the media listed in Table 1 was prepared in 100 ml quantities.

The media were adjusted to pH 6.8 before autoclaving. The media were inoculated with an 8 hour culture of NRRL-B-18050 at a rate of 1% and then incubated at 35° C. for 18 hours. After 18 hours, 25 ml of the above culture were centrifuged at 12,000 ×g for 10 minutes at 4° C. The supernatant was then filter sterilized using a 0.22 microns filter (Millipore, Bedford, Mass.) and tested for the least dilution (titer) which inhibited *Pediococcus pentosaceus* FBB63C as the indicator strain.

The results of the nutritional study are summarized in Table 1.

TABLE 1

NUTRITIONAL STUDIES OF NRRL-B-18050 FOR THE PRODUCTION OF BACTERIOCIN PA-1

| Media | Titer |
|---|---|
| MRS lactobacillus broth (Difco, Detroit, MI) | 1:4+ |
| MRS + 2% yeast extract (Oxoid, Basingstoke, England) | 1:8+ |
| MRS + 1% HY-CASE ™ (Sheffield Products, Norwich, NY) | 1:4+ |
| MRS + 1% HY-SOY ™ (Sheffield Products, Norwich, NY) | 1:4+ |
| MRS + 1% casamino acids (Difco, Detroit, MI) | 1:4 |
| MRS + 2% yeast extract + 1% HY-CASE ™ | 1:4 |
| MRS + 2% yeast extract + 1% HY-SOY ™ | 1:4 |
| MRS + 2% yeast extract + 1% casamino acids | 1:8+ |
| MRS BASE (lab formulation containing all components of MRS except proteose peptone) | |
| (a) with 1% HY-CASE ™ | 1:4 |
| (b) with 1% HY-SOY ™ | 1:4+ |
| 1% HY-CASE ™<br>2.5% yeast extract<br>2.0% glucose | 1+ |
| 1% HY-SOY ™<br>2.5% yeast extract<br>2.0% glucose | 1+ |
| 1.2% HY-CASE ™<br>1.2% HY-SOY ™ 2.0% yeast extract<br>5.0% glucose | 1 |
| 6% whey<br>1% glucose | 0 |
| 6% whey<br>1% glucose<br>2% yeast extract | 1:2 |
| 6% whey<br>1% glucose<br>2% casamino acids | 1:2+ |
| 6% whey<br>1% glucose<br>2% yeast extract<br>2% casamino acids | 1:2 |
| 10% peptonized milk with: | |
| (a) 2.0% yeast extract and .5% glucose | 1:4+ |
| (b) 2.0% yeast extract and 1% glucose | 1:4+ |
| (c) 2.0% yeast extract with 2% glucose | 1:4+ |
| 10% peptonized milk with: | |
| (a) 2% yeast extract with 0.5% galactose | 1+ |
| (b) 2% yeast extract with 1% galactose | 1:2+ |
| CORN STEEP BASE | |
| 4% cornsteep<br>5% glucose and<br>3% yeast extract with: | |
| (a) with 1% HY-CASE ™ | 1:4+ |
| (b) with 2% HY-CASE ™ | 1:4 |
| (c) with 1% HY-SOY ™ | 1:2+ |
| (d) with 2% HY-SOY ™ | 1:4 |
| (e) with 1% peptonized milk nutrient (Sheffield Products, Norwich, NY) | 1:4 |
| (f) with 1% N-Z AMINE TYPE AS ™ (Sheffield Products, Norwich, NY) | 1:2+ |
| (g) with 1% PEPTICASE ™ (Sheffield Products, Norwich, NY) | 1:4 |
| (h) with 1% PRIMATONE ™ (Sheffield Products, Norwich, NY) | 1:4 |
| (i) with 1% PRIMAGEN ™ (Sheffield Products, Norwich, NY) | 1:2+ |
| (j) with 1% ALBUTONE ™ (Sheffield Products, Norwich, NY) | 1:2+ |
| (k) with 1% EDAMIN TYPE S ™ (Sheffield Products, Norwich, NY) | 1:2+ |
| (l) with 1% TRYPTONE ™ (Difco, Detroit, MI) | 1:2+ |
| CORN STEEP BASE | |
| 4% cornsteep<br>5% glucose; and | |

TABLE 1-continued
NUTRITIONAL STUDIES OF NRRL-B-18050 FOR THE PRODUCTION OF BACTERIOCIN PA-1

| Media | Titer |
|---|---|
| 3% yeast extract: | |
| (a) with 1% HY-CASE ™ 0.2% ammonium citrate | 1:4 |
| (b) with 1% HY-CASE ™ 0.5% sodium citrate | 1:4 |
| (c) with 1% HY-CASE ™ 0.01% MgSO$_4$ | 1:2+ |
| (d) with 1% HY-CASE ™ 0.005% MnSO$_4$ | 1:2+ |

(1)HY-CASE ™, HY-SOY ™, N-Z AMINE TYPE AS ™, PEPTICASE ™, PRIMATONE ™, PRIMAGEN ™, ALBUTONE ™, EDAMIN TYPE S ™ and TRYPTONE ™ are protein supplements.

The most effective medium for the production of bacteriocin PA-1 appears to be MRS broth supplemented with 2% yeast extract. Other media were not as effective, however protein supplements generally appear to stimulate bacteriocin production. Whey based media were the least effective for the production of bacteriocin PA-1.

EXAMPLE 2

Production of Dried Bacteriocin PA-1

*Pediococcus acidilactici* NRRL-B-18050 was grown overnight at 35° C. in 1 liter MRS broth supplemented with 2% yeast extract (Difco, Detroit, Mich.). The cells were pelleted by centifugation and supernatant was collected. Nonfat dry milk powder was added to 10% (weight/volume) to facilitate drying. This mixture then was lyophilized into a dry powder.

EXAMPLE 3

Activity of the bacteriocin (PA-1) from Pediococcus acidilactici NRRL-B-18050 against *Listeria monocytogenes* in Dressed Cottage cheese

*Listeria monocytogenes* was added to dressed Cottage cheese (pH 5.1) at a rate of $6.5 \times 10^3$ cfu/gram of dressed Cottage cheese. The bacteriocin powder to Example 1 (PA-1) was added to the Cottage cheese at a rate of 10 or 50 U (units)/g dressed Cottage cheese. The samples were mixed and incubated at 4° C. and aliquots were removed and plated onto McBride's Agar (Difco, Detroit, Mich.) and incubated at 32° C. and examined for growth of *Listeria monocytogenes*.

The results are shown in Table 2.

TABLE 2

| Sample | Contents | Growth of Listeria at 24 h |
|---|---|---|
| A | — | 0 |
| B | LM[1] | $7.5 \times 10^3$ cfu/g |
| C | PA-1, 50 U/g | 0 |
| D | LM[1]; PA-1, 10U/g | 0 |
| E | LM[1]; PA-1, 50U/g | 0 |

[1]LM = Listeria monocytogenes at $6.5 \times 10^3$ cells per gram.

EXAMPLE 4

Activity of the Bacteriocin (PA-1) against *Listeria monocytogenes* in Half and Half Cream

*Listeria monocytogenes* was added to the cream (pH 6.7) at a rate of $4.3 \times 10^3$ cfu/ml of cream. The bacteriocin powder PA-1 was added to the cream at a rate of 10 or 50 U/ml cream. The samples were mixed and incubated at 4° C. and aliquots were removed and examined for growth of *Listeria monocytogenes*.

The results are shown in Table 3.

TABLE 3

| Sample | Contents | Growth of Listeria at 24 h |
|---|---|---|
| A | — | 0 |
| B | LM[1], | $2.2 \times 10^3$ cfu/g |
| C | LM[1], PA,1, 50U/ml | 0 |

[1]LM = Listeria monocytogenes at $4.3 \times 10^3$ cells per ml.

EXAMPLE 5

Activity of Bacteriocin (PA-1) against *Listeria monocytogenes* in cheese sauce

*Listeria monocytogenes* was added to the cheese sauce (pH 5.25) at a rate of $5.3 \times 10^3$ cfu/g of cheese sauce. The bacteriocin powder PA-1 was added to the cheese sauce at a rate of 10 or 50 U/g of sauce. The samples were mixed and incubated at 4° C. and aliquots were removed and examined for growth of *Listeria monocytogenes*. The resutls are shown in Table 4.

TABLE 4

| Sample | Contents | Growth of Listeria at 24 h |
|---|---|---|
| A | — | 0 |
| B | LM[1], | $2.0 \times 10^4$ cfu/g |
| C | LM[1]; PA-1, 10U/g | $4.0 \times 10^2$ cfu/g |
| D | LM[1]; PA-1, 50U/g | 0 |

[1]LM = Listeria monocytogenes at $5.3 \times 10^3$ cells per gram.

As can be seen from Examples 3 to 5, the bacteriocin PA-1 was effective in controlling the growth of *Listeria monocytogenes* in food systems at various pH values. In the cream, Example 4, the pH was initially 6.7 and the Listeria were inhibited. In the cheese sauce Example 5, the pH was slightly acidic at a pH of 5.25. In both of the above examples and the Cottage cheese example, *Listeria monocytogenes* was inhibited.

EXAMPLE 6

Effect of the bacteriocin powder PA-1 on an exponential culture of *Listeria monocytogenes*

Sterile PA-1 bacteriocin powder was added to an exponential culture of *Listeria monocytogenes* at a rate of 200 U/ml of broth and 500 U/ml of broth. *Listeria monocytogenes* was grown in APT broth at 32° C. Absorbance was followed over time at 660 nm. FIG. 1 shows that when the sterile powder was added to the culture after 3.75 hours, the absorbance at 660 nm began to decrease, whereas the control flask continued to grow and increase in turbidity thus indicating that bacteriocin PA-1 was not only inhibitory but also bacteriocidal for *Listeria monocytogenes*.

EXAMPLE 7

Minimum inhibitory concentration (MIC) and minimum bacteriocidal concentration (MBC) of the bacteriocin PA-1 against *Listeria monocytogenes*

Bacteriocin PA-1 powder was dissolved in APT broth and two-fold serially diluted to concentrations ranging from 1000 U/ml to 2.0 U/ml. Approximately $1 \times 10^3$ *Listeria monocytogenes*/ml were added to each of the tubes which then were incubated for 24 hours at 32° C. The MIC value was the lowest concentration tube displaying no visible turbidity. The MBC value was the lowest concentration tube which when plated onto APT agar showed no colony forming units (CFU's). The results are summarized in Table 5.

TABLE 5

| Strain | MIC | MBC |
|---|---|---|
| Listeria monocytogenes LM01 | <2.0 U/ml | 7.8 U/ml |
| Pediococcus pentosaceus FBB63C | 7.8 U/ml | 31.3 U/ml |

As indicated in Table 5, Listeria monocytogenes is quite sensitive to PA-1 bacteriocin, even more so than the indicator P. pentosaceus strain FBB63C.

EXAMPLE 8

Plasmid DNA was isolated from Pediococcus acidilactici NRRL-B-18050, and DNA samples were subjected to agarose gel electrophoresis as previously described (Gonzalez, C. F., and B. S. Kunka, Appl. Environ. Microbiol. 46:81–89 (1983)). A restriction map as shown in FIG. 2 of the plasmid pSRQ11 was obtained by combinations of the following procedures: (i) analysis of DNA fragments obtained after digestion with two enzymes and (ii) analysis of the fragments on 0.7% agarose and 5.0% polyacrylamide gel electrophoresis.

Based on the approximate size of the bacteriocin PA-1 of 16,500 daltons, the gene for the bacteriocin PA-1 appears to be encoded on a 450 bp segment on the plasmid pSRQ11, between the NdeI site at 1.6 kb and the 3.2 kb ClaI site (FIG. 2).

The bacteriocin (PA-1) was effective even at pH values which were near neutrality. The observation that the bacteriocin (PA-1) inhibits Listeria monocytogenes was unexpected because (i) Listeria monocytogenes is a human pathogen (ii) the ecological niche of Listeria monocytogenes is not similar to Pediococcus acidilactici.

It is intended that the foregoing description be only illustrative of the present invention and that the present invention be limited only by the hereinafter appended claims.

We claim:

1. A method for inhibiting growth of Listeria monocytogenes in an unspoiled material which can be contaminated with the Listeria monocytogenes which comprises:

providing a bacteriocin in an unspoiled material in an effective amount which inhibits the Listeria monocytogenes, wherein the bacteriocin is derived from a Pediococcus acidilactici containing DNA derived from a plasmid measuring about 9.4 kilobase pairs in molecular size which encodes for the production of the bacteriocin and wherein the bacteriocin inhibits the Listeria monocytogenes in a pH range between about pH 4 to 9.

2. The method of claim 1 wherein the Pediococcus acidilactici is Pediococcus acidilactici NRRL-B-18050.

3. The method of claim 1 where the bacteriocin has a molecular weight of about 16,500 daltons and is inactivated by in vitro mixing with protease, papain or alpha-chymotrypsion and is unaffected by phospholipase C, lysozyme, DNase and RNase or heating to 100° C. in water and wherein the bacteriocin inhibits the Listeria monocytogenes in a pH range between about pH 4 to 9.

4. The method of claim 1 wherein the bacteriocin is produced in an aqueous solution derived from a growth medium for the Pediococcus acidilactici and wherein the growth medium contains an amino acid source which enhances the production of the bacteriocin.

5. The method of claim 4 wherein the amino acid source in the growth medium is yeast extract.

6. The method of claim 4 wherein the aqueous solution is dried in the presence of a food grade drying aid to a flowable powder which is added to the food.

7. The method of claim 6 wherein the drying aid is non-fat dry milk.

8. The method of claim 7 wherein the flowable powder contains between about 1 and 100,000 AU per gram.

9. The method of claim 8 wherein the Pediococcus acidilactici is Pediococcus acidilactici NRRL-B-18050.

10. The method of claim 6 wherein the Pediococcus acidilactici is Pediococcus acidilactici NRRL-B-18050.

11. The method of claim 4 wherein the Pediococcus acidilactici is Pediococcus acidilactici NRRL-B-18050.

12. The method of claim 1 wherein the bacteriocin is a powder which is produced by drying an an aqueous growth medium incubated with the Pediococcus acidilactici.

13. The method of claim 1 wherein the bacteriocin is produced by membrane filtration of a growth medium containing the bacteriocin from growth of the Pediococcus acidilactici to remove low molecular weight compounds from the growth medium.

14. The method of claim 13 wherein the bacteriocin is in the form of a lyophilized powder.

15. The method of claim 1 wherein the bacteriocin is separated from an aqueous growth medium containing the bacteriocin from growth of the Pediococcus acidilactici in the growth medium and then the bacteriocin is dried.

16. The method of claim 1 wherein the DNA is the 9.4 kilobase plasmid.

17. A method for inhibiting growth of Listeria monocytogenes in an unspoiled food which can contain the Listeria monocytogenes as a contaminant which comprises:

adding a bacteriocin into an unspoiled food in an effective amount which inhibits the Listeria monocytogenes, wherein the bacteriocin is derived from a Pediococcus acidilactici containing DNA derived from a plasmid measuring about 9.4 kilobase pairs in molecular size which encodes for the production of the bacteriocin and wherein the bacteriocin inhibits the Listeria monocytogenes in a pH range between about pH 4 9.

18. The method of claim 17 wherein the bacteriocin which is added to the food is in an aqueous growth medium incubated with the Pediococcus acidilactici.

19. The method of claim 17 wherein the bacteriocin is produced in an aqueous growth medium incubated with the Pediococcus acidilactici and then the aqueous growth medium is dried to a flowable powder with or without a food grade drying aid and wherein the flowable powder is added to the food.

20. The method of claim 17 wherein the food contains between about 1 and 100,000 AU of the bacteriocin per gram of food.

21. The method of claim 17 wherein the food contains milk of a milk derivative.

22. The method of claim 17 wherein the food is a prepared salad.

23. The method of claim 17 wherein the food is or contains meat.

24. The method of claim 17 wherein the food is or contains cheese.

25. The method of claim 17 wherein the food is or contains Cottage cheese.

26. The method of claim 17 wherein the food is selected from an ice milk or ice cream.

* * * * *

UNITED STATES PATENT AND TRADEMARK OFFICE
CERTIFICATE OF CORRECTION

PATENT NO. : 4,929,445

DATED : May 29, 1990

INVENTOR(S) : Peter A. Vandenbergh, Michael J. Pucci, Blair S. Kunka and Ebenezer R. Vedamuthu It is certified that error appears in the above—identified patent and that said Letters Patent is hereby corrected as shown below:

Column 1, line 64, "Accoding" should be --According--.

Column 2, line 11 "becomes" should be --become--.

Column 2, line 23, "used are O" should be --used are ●-- and "(no PA-1 added); ●," should be --(no PA-1 added); O,--.

Column 2, line 28 "pSQ11" should be --pSRQ11--

Column 2, line 58 "spcies" should be --species--.

Column 3, line 19 "1,000,000" should be --100,000--.

Column 3, line 21 "Once" should be --One--.

Column 3, line 29, "cream of" should be --cream or--.

Column 3, line 50, "10850" should be --18050--.

UNITED STATES PATENT AND TRADEMARK OFFICE
CERTIFICATE OF CORRECTION

PATENT NO. : 4,929,445
DATED : May 29, 1990
INVENTOR(S) : Peter A. Vandenbergh, Michael J. Pucci, Blair S. Kunka and Ebenezer R. Vedamuthu It is certified that error appears in the above—identified patent and that said Letters Patent is hereby corrected as shown below:

Column 5, line 31 "centifugation" should be --centrifugation--. After "and" insert --the--.

Column 5, line 42 "to Example 1" should read --of Example 1--.

Column 6, line 23 "resutls" should be --results--.

Column 7, line 55 "where" should be --wherein--.

Column 7, line 58 "chymotrypsion" should be --chymotrypsin--.

Column 8, line 15 "an", second occurrence, should be deleted.

Column 8, line 43, "pH 49" should read --pH 4 to 9--.

Signed and Sealed this

Second Day of June, 1992

*Attest:*

DOUGLAS B. COMER

*Attesting Officer*   *Acting Commissioner of Patents and Trademarks*